(12) United States Patent
Leo et al.

(10) Patent No.: US 8,090,540 B2
(45) Date of Patent: Jan. 3, 2012

(54) METHOD FOR DESIGNING 3-DIMENSIONAL POROUS TISSUE ENGINEERING SCAFFOLD

(75) Inventors: Chin Sim Leo, Singapore (SG); Chi Mun Cheah, Singapore (SG)

(73) Assignee: Nanyang Polytechnic, Singapore (SG)

( * ) Notice: Subject to any disclaimer, the term of this patent is extended or adjusted under 35 U.S.C. 154(b) by 1458 days.

(21) Appl. No.: 11/239,008

(22) Filed: Sep. 30, 2005

(65) Prior Publication Data

US 2006/0129328 A1 Jun. 15, 2006

(30) Foreign Application Priority Data

Dec. 10, 2004 (SG) ................ 200407332-6

(51) Int. Cl.
 *G01N 33/48* (2006.01)
 *G06G 7/48* (2006.01)
 *G06G 7/58* (2006.01)
 *G01N 1/00* (2006.01)

(52) U.S. Cl. ............... 702/19; 703/11; 712/220; 422/50

(58) Field of Classification Search ....................... None
See application file for complete search history.

(56) References Cited

U.S. PATENT DOCUMENTS

| 5,990,904 | A | * | 11/1999 | Griffin | 345/631 |
| 6,501,481 | B1 | * | 12/2002 | Wood et al. | 345/582 |
| 7,133,041 | B2 | * | 11/2006 | Kaufman et al. | 345/419 |

* cited by examiner

*Primary Examiner* — Eric S Dejong
(74) *Attorney, Agent, or Firm* — Pyprus Pte Ltd

(57) ABSTRACT

The present invention provides a method for designing three-dimensional scaffold structures that are anatomically accurate and possess the necessary internal porous micro-architecture design, wherein the porous micro-architecture is necessary for the proliferation and colonization of cultured cells that lead to tissue formation. The design method of the present invention utilizes the patient data derived from medical imaging modalities (e.g., CT or MRI) in combination with computer data manipulation techniques. The present invention further provides that the resultant scaffold design can be easily manufactured by Rapid Prototyping fabrication techniques.

9 Claims, 5 Drawing Sheets

METHOD FOR DESIGNING 3-DIMENSIONAL POROUS TISSUE ENGINEERING SCAFFOLD

FIELD OF THE INVENTION

The present invention generally relates to methods of designing and fabricating three-dimensional scaffolds, and more particularly to methods of designing and fabricating a three-dimensional porous scaffold by using bitmap templates.

BACKGROUND OF THE INVENTION

Designing and fabricating three-dimensional scaffolds are essential for tissue engineering. For implantable scaffolds, it is desirable to have internal pores and internal channels connecting the internal pores, so that the cells can migrate into the pores and channels and grow therein, resulting in better compatibility of the scaffolds with their host.

There have been attempts to manually model the micro-architecture within a scaffold by using traditional CAD modeling techniques before committing the models for Rapid Prototyping fabrication. However, there are many limitations of employing traditional CAD techniques for modeling the geometry and micro-architecture of tissue engineering scaffolds. The limitations include: highly labor intensive and lengthy; computational resource intensive; and requirement of skilled CAD personnel because the process is not automated.

Therefore, there is an imperative need to develop methods for designing and fabricating a three-dimensional porous scaffold by eliminating or reducing one or more of the limitations associated with the current methods. This invention satisfies this need by disclosing methods of designing and fabricating a three-dimensional porous scaffold by using bitmap templates. Other advantages of this invention will be apparent with reference to the detailed description.

SUMMARY OF THE INVENTION

The present invention provides a method for designing three-dimensional scaffold structures that are anatomically accurate and possess the necessary internal porous micro-architecture design, wherein the porous micro-architecture is necessary for the proliferation and colonization of cultured cells that lead to tissue formation. The design method of the present invention utilizes the patient data derived from medical imaging modalities (e.g., CT or MRI) in combination with computer data manipulation techniques. The present invention further provides that the resultant scaffold design can be easily manufactured by Rapid Prototyping fabrication techniques.

In one aspect of the present invention, there is provided a method for designing a three-dimensional porous scaffold with internal pores and internal channels connecting the internal pores. The method comprises steps of generating bitmap templates according to the desired shapes and dimensions of the pores and channels within the scaffold; the bitmap templates having grids and spacings between the grids; pre-processing two-dimensional images to obtain the required structure in each image; duplicating the processed images, wherein the duplicated images are used to fill the slice thicknesses between two consecutive images; performing Boolean operation between the bitmap templates and the images including the pre-processed and duplicated, thereby the grid pattern of the bitmap templates will be transferred onto the images and will appear as two-dimensional array of pores and channels; and converting the series of two-dimensional images into STL format; thereby the three-dimensional porous scaffold is designed. In one embodiment, the number of different bitmap templates depends on the complexity of the pores and channels. In another embodiment, the width of the grids and spacings are determined by the shape and dimension of the pores and channels. In yet another embodiment, the pre-processing uses a thresholding process for filtering unwanted data. In still another embodiment, the number of duplicates for each slice depends upon the resolution of the DICOM image, the required pore size, or the thickness of the slices. In yet still another embodiment, the intersection between the bitmap templates and the images is determined by the pixel intensity of the bitmap.

In another aspect of the present invention, there is provided a method for fabricating a three-dimensional porous scaffold with internal pores and internal channels connecting the internal pores. The method comprises steps of generating bitmap templates according to the desired shapes and dimensions of the pores and channels within the scaffold; the bitmap templates having grids and spacings between the grids; pre-processing two-dimensional images to obtain the required structure in each image; duplicating the processed images, wherein the duplicated images are used to fill the slice thicknesses between two consecutive images; performing Boolean operation between the bitmap templates and the images including the pre-processed and duplicated, thereby the grid pattern of the bitmap templates will be transferred onto the images and will appear as two-dimensional array of pores and channels; converting the series of two-dimensional images into STL format; thereby the three-dimensional porous scaffold is designed; and fabricating the three-dimensional porous scaffold according to the STL format of the scaffold design. In one embodiment of the method, the fabrication method includes free-form prototyping.

The objectives and advantages of the invention will become apparent from the following detailed description of preferred embodiments thereof in connection with the accompanying drawings.

BRIEF DESCRIPTION OF THE DRAWINGS

Preferred embodiments according to the present invention will now be described with reference to the Figures, in which like reference numerals denote like elements.

FIG. 5b shows the negative of the bitmap template shown in FIG. 5a.

FIG. 5d shows the result of intersecting the Medical Image of FIG. 3 with the bitmap template as shown in FIG. 5a.

DETAILED DESCRIPTION OF THE INVENTION

The present invention may be understood more readily by reference to the following detailed description of certain embodiments of the invention.

Throughout this application, where publications are referenced, the disclosures of these publications are hereby incorporated by reference, in their entireties, into this application in order to more fully describe the state of art to which this invention pertains.

The present invention provides methods for designing and fabricating a three-dimensional porous scaffold. Briefly, the methods use specially laid out bitmap templates to create the internal micro-architecture of the intended scaffold designs. The bitmap templates generated consist of uniform arrays of grids representing the internal structure of the scaffold and the voids in between the structures. A wide variety of bitmap templates can be created by changing the size, spacing and shape of the grids to give rise to different scaffold internal micro-architecture designs which possess different microstructural properties (e.g., porosity, pore shape and distribution and interconnectivity) to suit various Tissue Engineering applications. Patient data is acquired through the use of computer based medical imaging systems (e.g., CT, MRI). The output of such imaging systems is a collection of two-dimensional image slices (tomogram) which are stored in DICOM file format. Each image slice is separated by a fixed user determined interval known as the slice thickness. The slice thickness directly affects the resolution and accuracy of any three-dimensional models generated using the imaging data slices as an input.

To create the internal porous micro-architecture of the scaffolds, the imaging data slices are firstly modified by intersecting them with appropriately selected bitmap templates via Boolean operation. This will result in the transferring of the grid pattern on the bitmap template onto the image slice. To reconstruct the three-dimensional profile of the scaffold structure, the internal (micro-architecture) and external (external geometry) contour data of the modified image slices are extracted. Surface patching technique is then applied between the contours to create a three-dimensional closed surface model of the scaffold.

Figure 1:
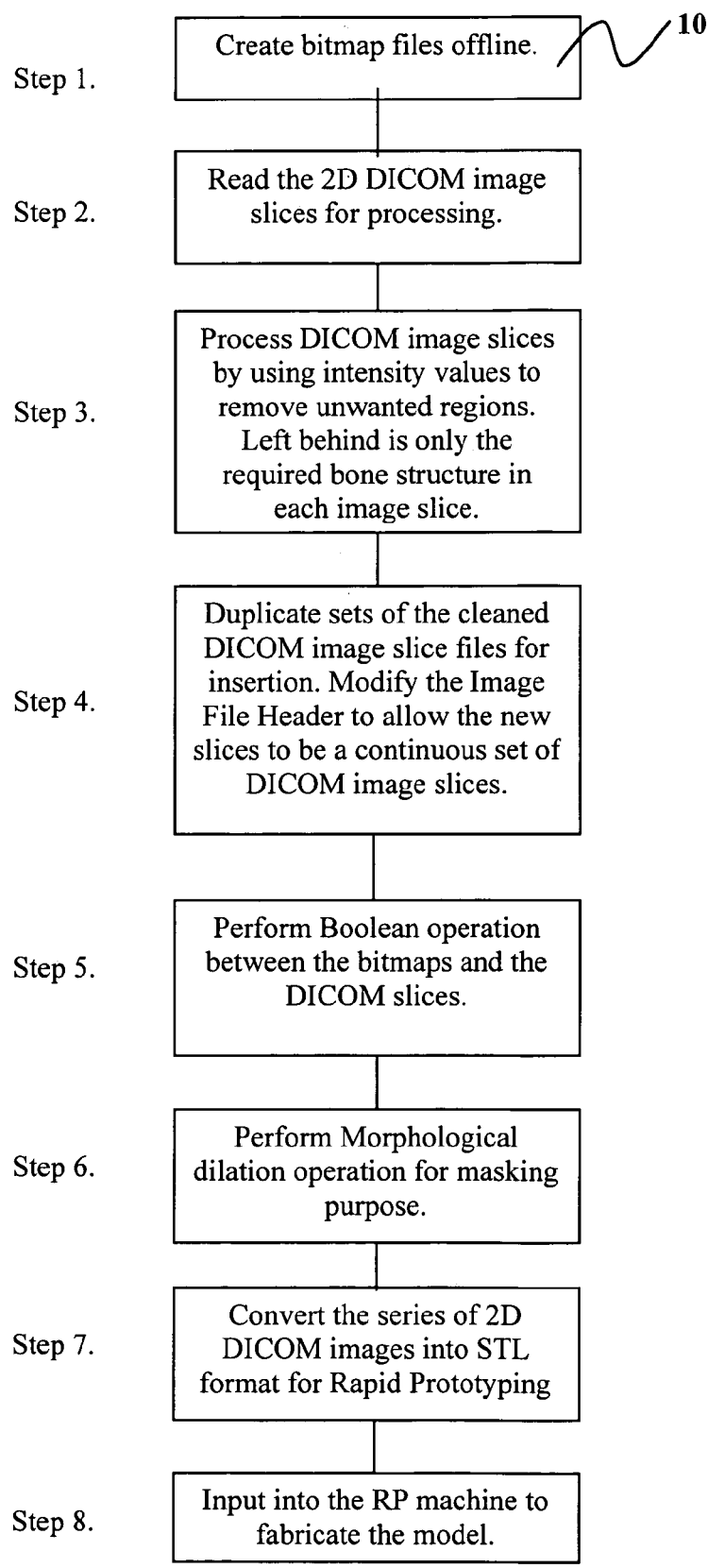
FIG. 1 is a flowchart showing the main steps of the designing and fabricating method of a three-dimensional porous scaffold.

Now there is provided a more detailed description of the methods for designing and fabricating a three-dimensional porous scaffold in accordance with one embodiment of the present invention. FIG. 1 is a flow chart showing the main steps of the methods. It is to be appreciated that while the following description will use specific computer terms and programs for the convenience of explanation, other computer programs may be used if they are applicable for the method of the present invention. In addition, the order of steps in the flow chart is designated only for the convenience of narration. The present invention can be practiced without following the order of steps depicted in FIG. 1. For example, the step 1 of creating bitmap files can be performed anytime before the Boolean operation.

Figure 5A:
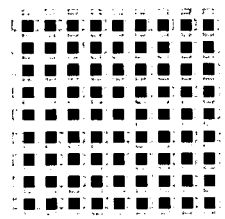
FIG. 5a shows one bitmap template.
Figure 5B:
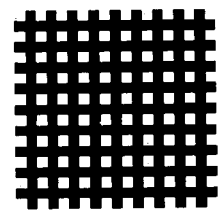
Figure 5C:
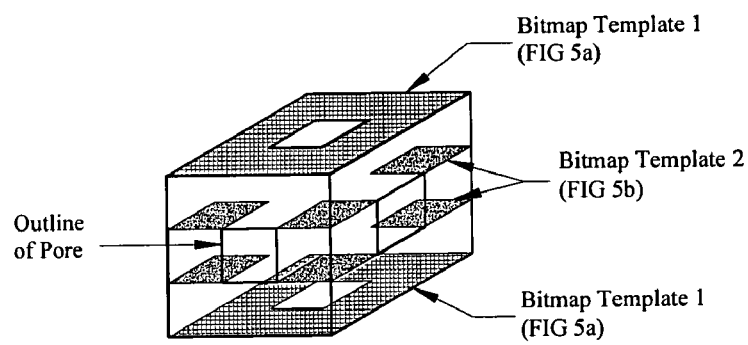
FIG. 5c shows a diagrammatic view of forming square pores by overlaying the bitmap templates of FIG. 5a and FIG. 5b.

Referring to FIG. 1, the method may start by creating bitmap templates offline 10. As discussed above, a three-dimensional porous scaffold comprises internal pores and internal channels connecting the internal pores. One aspect of the present invention is to utilize the bitmap templates to create the desired internal pores and channels. Thus, the bitmap templates are created according to the desired shapes and dimensions of the pores and channels within the scaffold. The number of different bitmap templates that have to be created for a scaffold depends on many factors including the size of the scaffold, the resolution of the medical images, the slice thickness, and the complexity of the pores and channels. For example, if a square-shaped pore is required, two different bitmap templates that are exact negatives of one another will be prepared, as shown in FIG. 5*a* and FIG. 5*b*. The three-dimensional square pore structure is then achieved by arranging the two different bitmap templates in an alternating manner, as shown in FIG. 5*c*. The shape and dimension of the pores and channels can be controlled by specifying the width of the grids and the spacing between the grids in the bitmap templates. It is apparent that the bitmap templates can be employed to create pores and channels within a scaffold with any shapes and complexity. However, creating pore shapes with more complex geometries demands more different bitmap templates and more complex arrangements of the different bitmap templates.

The creation of bitmap templates can be manual drawing of the template design by using any computer graphic software that supports a bitmap file format. A short algorithm can also be used to automatically generate the required bitmap templates. The methods and algorithms for generating and manipulating the bitmap templates are well known to those skilled in the art, so that no further details will be provided herein.

Figure 2:
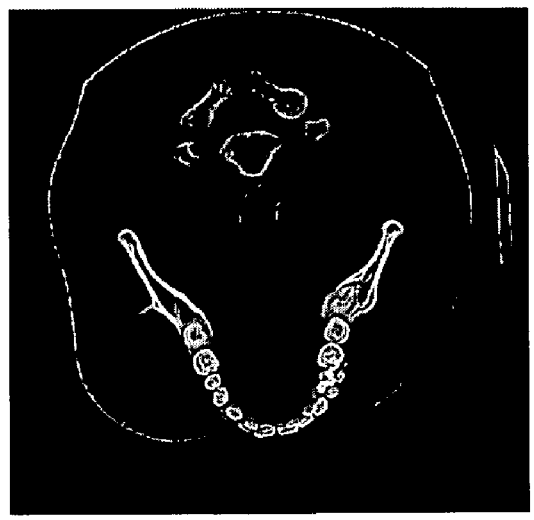
FIG. 2 shows a sample of the DICOM medical images.

In order to create the three-dimensional porous scaffold, two-dimensional images are prepared 20. While medical images from CT, MRI or Ultrasound are used to illustrate the application of the principles of the present invention, it is to be appreciated that the present invention is not so limited. The two-dimensional medical imaging slice data can be generated either by CT, MRI or other types of computer-based medical imaging systems. The generated image slices are stored using a standard file format known as the Digital Imaging and Communications in Medicine (DICOM). FIG. 2 shows a sample of the DICOM medical image. Each individual image slice is stored in a single DICOM file. As such, the scanned profile data of a patient is contained in a series of DICOM files, each showing a particular cross-section of the patient's body. The spacing between two consecutive image slices is known as the slice thickness that is determined by radiologists. The DICOM medical images may be generated by actual scanning or obtained from public databases.

Figure 3:
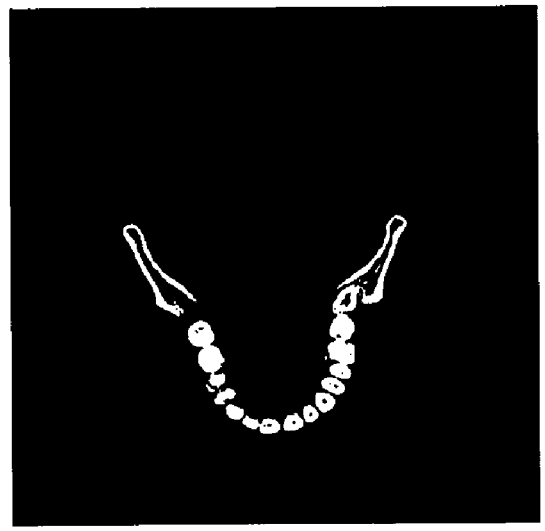
FIG. 3 shows a sample of the pre-processed medical image after having removed the unwanted data from the DICOM medical image as shown in FIG. 2.

Then the next step is to pre-process the DICOM files to remove unwanted Data from them 30. In a typical image slice, the different types of tissues captured by the imaging system are displayed as distinct regions with different pixel intensity. For generating a scaffold structure, only the profile of certain tissue/tissues (the tissue/tissues which the Tissue Engineered implants are going to replace) on each image slice corresponding to the region of interest is required. As such, each image slice will be pre-processed to isolate the required data and to remove all unwanted data. FIG. 3 shows a sample of the pre-processed medical image after having removed the unwanted data from the DICOM medical image as shown in FIG. 2.

The pre-process for categorizing of required and unwanted data from a DICOM file can be carried out in any possible ways. For example, using a thresholding process for filtering unwanted data, pixels with intensity value less than the threshold value as determined by a user are removed as shown below. As such, the threshold value should be set smaller than the intensity value of the pixels representing the required data.

$$f(x) = \begin{cases} 0 & \text{for } f(x) < \varepsilon, \text{ where } \varepsilon \text{ is the Threshold value} \\ f(x) & \text{otherwise} \end{cases}$$

The removal of unwanted data can also be carried out manually using a specially written algorithm or any image editing software that supports DICOM file format.

Figure 4:
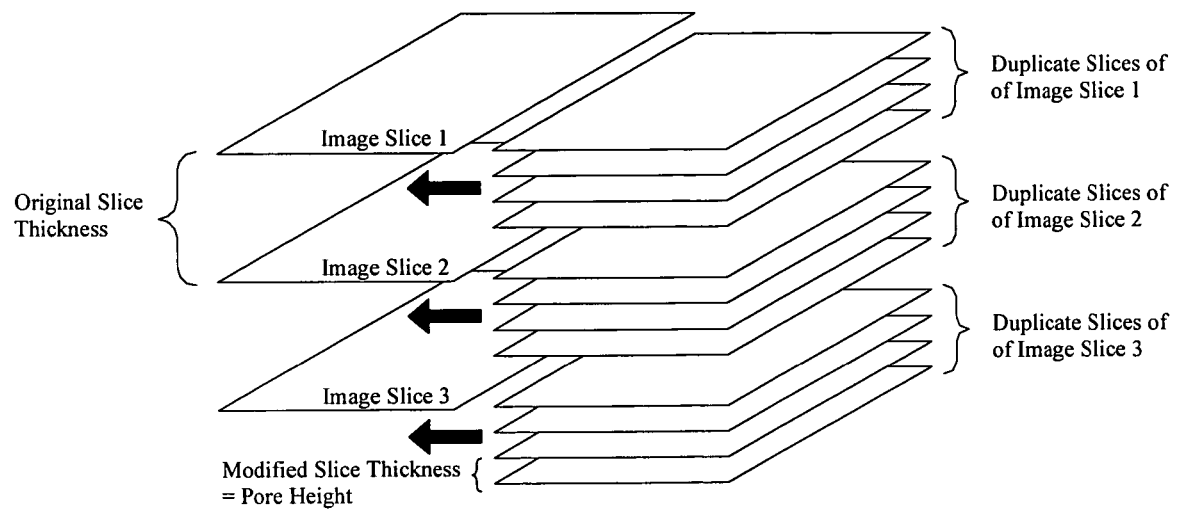
FIG. 4 is a diagram showing the refinement of the slice thicknesses.

As mentioned above, there is a slice thickness between two consecutive image slices. In order to use the pre-processed image slices to generate the three-dimensional structure, the slice thickness has to be refined. The refinement may be accomplished in many different ways. One exemplary refinement is shown in FIG. 4. The refinement is done by duplicating the sets of the pre-processed DICOM image slice files and filling the slice thicknesses by inserting the duplicated DICOM image slices into the slice thickness 40. The number of duplicates to be made for each slice is determined by the thickness of the pre-processed DICOM image slice and the slice thickness. After duplication, the image header data of all the slices has to be re-designated by the user. This modification is necessary to ensure that the inserted slices would be deemed as being a continuous set of 2D images.

Figure 5D:
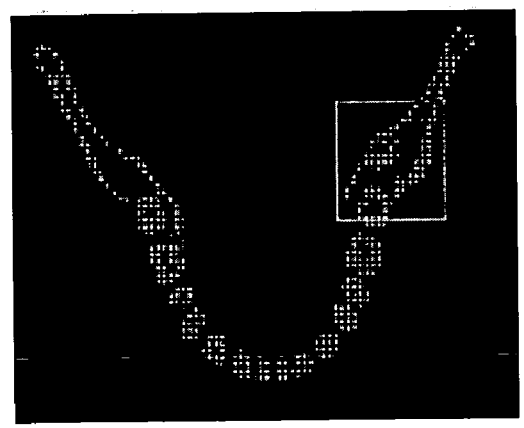

Referring still to FIG. 1, after the bitmap templates are created and the image slices are pre-processed, a Boolean intersection operation is then performed between the bitmap templates and the image slices 50. Using this operation, the grid pattern of the bitmap templates will be transferred onto the image slices and will appear as two-dimensional array of pores and channels. For example, as shown in FIGS. 5a and 5b, two sets of bitmap templates being exact negatives of one another are used to generate the squared pores and channels as illustrated in FIG. 5c. FIG. 5d shows the result of intersecting the Medical Image of FIG. 3 and the Bitmap Template 1 of FIG. 5a. Different bitmap templates for intersection with the image slices will be required for different geometrical shape and size of the pores generated in the scaffold structure.

Figure 6A:
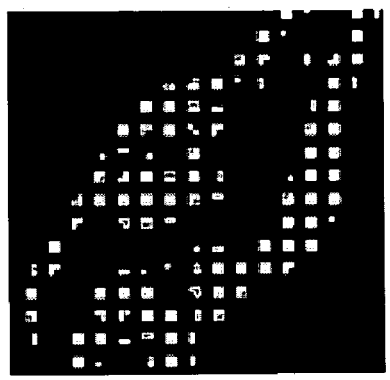
FIGS. 6a and 6b show an enlarged part of the image of FIG. 5d before and after the morphological operation.
Figure 6B:
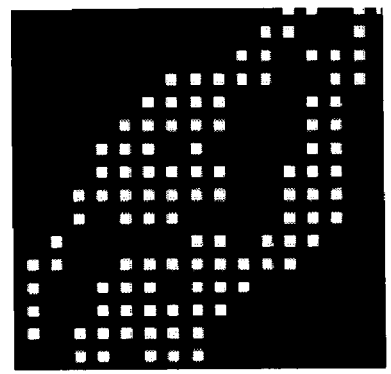

For cases where the pore size is represented by n×n (n>1) pixels, intersection of the image slices with the bitmap templates may result in the generation of incompletely-formed pores at the edges of the region of interest. If such incomplete pores are not removed from the image slices, they will result in the formation of loose ends of materials sticking out from the scaffold structure during the fabrication process. Such loose ends of materials are not desirable as they can be easily broken off. Thus, a morphological operation is carried out to remove the incomplete pores 60. This operation checks, identifies and removes all incomplete pores within the image. If an incompletely-formed pore is detected, the intensities of the pixels representing the body of material surrounding the incomplete pore are set to zero (empty space), thereby removing the incomplete pore. FIGS. 6a and 6b show an enlarged part of the image of FIG. 5d before and after the morphological operation.

Figure 7:
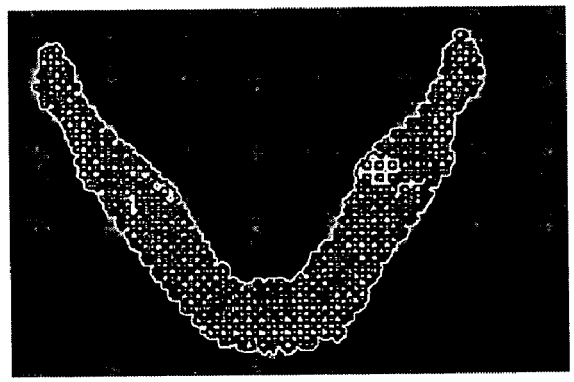
FIG. 7 shows the constructed three-dimensional structure of the image of FIG. 3 in STL file.

The final step 70 of the designing process is to convert the two-dimensional image slices into three-dimensional computer representations of the scaffold models. The three-dimensional computer representation depends on the selected fabrication method for the scaffold. For example, the scaffold can be a format that can be accepted by the Rapid Prototyping machine to fabricate the porous scaffold. For this step, the modified set of DICOM files can be input into a three-dimensional modeling software that supports DICOM file format for conversion. FIG. 7 shows the constructed three-dimensional structure of the image of FIG. 3 that is represented by using the exemplary STL as the output file format for the three-dimensional reconstruction process.

Upon having obtained the STL file, the scaffold can be fabricated 80. There are many available fabricating techniques that can be used for fabricating the designed scaffold. The exemplary fabricating techniques include Inkjet printing described by Sanders Jr. et al. in U.S. Pat. No. 5,506,607; Stereolithography described by Hull et al. in U.S. Pat. No. 4,575,330; and Laser Sintering described by Deckard et al. in U.S. Pat. No. 4,863,538.

Figure 8:
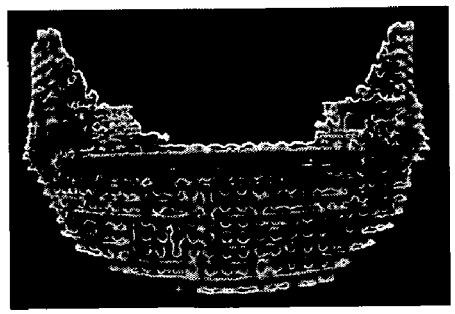
FIG. 8 shows a scaffold around the jaw area fabricated by a Rapid Prototyping machine.

FIG. 8 shows a scaffold around the jaw area fabricated by a Rapid Prototyping machine.

The materials that are applicable for the present invention are not limited to any specific type. It could be biodegradable if the scaffold is to be used in providing a support for tissue growth in vivo. It could be ceramic, plastic, polymers, metals, and alloys if the scaffold is to be used as implant. The selection of a specific material or materials for making a scaffold depends upon the characteristics of the desired scaffold.

While the present invention has been described with reference to particular embodiments, it will be understood that the embodiments are illustrative and that the invention scope is not so limited. Alternative embodiments of the present invention will become apparent to those having ordinary skill in the art to which the present invention pertains. Such alternate embodiments are considered to be encompassed within the spirit and scope of the present invention. Accordingly, the scope of the present invention is described by the appended claims and is supported by the foregoing description.

What is claimed is:

1. A method for fabricating a three-dimensional porous scaffold with internal pores and internal channels connecting the internal pores, comprising:
   generating bitmap templates according to the desired shapes and dimensions of the pores and channels within the scaffold; the bitmap templates having grids and spacings between the grids;
   pre-processing two-dimensional images to obtain the required structure in each image;
   duplicating the processed images, wherein the duplicated images are used to fill the slice thicknesses between two consecutive images;
   performing Boolean operation between the bitmap templates and the images including the pre-processed and duplicated, thereby the grid pattern of the bitmap templates will be transferred onto the images and will appear as two-dimensional array of pores and channels;
   converting the series of two-dimensional images into STL format; thereby the three-dimensional porous scaffold is designed; and
   fabricating the three-dimensional porous scaffold according to the STL format of the scaffold design.

2. The fabricating method of claim 1, wherein, in the step of generating the bitmap templates, the number of different bitmap templates depends on the complexity of the pores and channels.

3. The fabricating method of claim 1, wherein, in the step of generating the bitmap templates, the width of the grids and spacings are determined by the shape and dimension of the pores and channels.

4. The fabricating method of claim 1, wherein, in the step of pre-processing the two-dimensional images, the pre-processing uses a thresholding process for filtering unwanted data.

5. The fabricating method of claim 1, wherein, in the step of duplicating the pre-processed images, the number of duplicates for each slice depends upon the resolution of a DICOM image, the required pore size, or the thickness of the slices.

6. The fabricating method of claim 1, wherein, in the step of performing Boolean operation between the bitmap templates and the images, the intersection between the bitmap templates and the images is determined by the pixel intensity of the bitmap.

7. The fabricating method of claim 1, wherein the two-dimensional images may be medical image slices taken by CT, MRI, Ultrasound or other computer-based medical imaging systems.

8. The fabricating method of claim 1, optionally further comprising:

performing a morphological modification to check, identify and remove all incomplete pores within the image.

9. The fabricating method of claim 1, wherein, during the step of fabricating the scaffold, the technique includes free-form prototyping.

* * * * *